(12) United States Patent
Nakajima et al.

(10) Patent No.: US 8,075,529 B2
(45) Date of Patent: Dec. 13, 2011

(54) INDWELLING NEEDLE ASSEMBLY

(75) Inventors: Hiroaki Nakajima, Narashino (JP); Toshikazu Ohashi, Hyuga (JP)

(73) Assignees: Medikit Co., Ltd., Tokyo (JP); Togo Medikit Co., Ltd., Tokyo (JP)

( * ) Notice: Subject to any disclaimer, the term of this patent is extended or adjusted under 35 U.S.C. 154(b) by 0 days.

(21) Appl. No.: 12/000,891

(22) Filed: Dec. 18, 2007

(65) Prior Publication Data

US 2008/0147010 A1 Jun. 19, 2008

(30) Foreign Application Priority Data

Dec. 18, 2006 (JP) ................ P2006-340501
Dec. 11, 2007 (JP) ................ P2007-319259

(51) Int. Cl.
*A61M 5/178* (2006.01)
*A61M 25/00* (2006.01)

(52) U.S. Cl. ......... 604/164.11; 604/164.09; 604/164.01; 604/164.12; 604/264; 604/523; 604/168.01; 604/164.06

(58) Field of Classification Search .............. 604/11, 604/171, 93.01–285, 523
See application file for complete search history.

(56) References Cited

U.S. PATENT DOCUMENTS

| | | | |
|---|---|---|---|
| 3,565,074 A | | 2/1971 | Foti |
| 3,811,440 A | * | 5/1974 | Moorehead et al. ..... 604/167.01 |
| 4,994,027 A | * | 2/1991 | Farrell ................ 604/510 |
| 5,242,410 A | * | 9/1993 | Melker .................. 604/164.1 |
| 5,336,176 A | * | 8/1994 | Yoon ....................... 604/506 |
| 5,380,292 A | | 1/1995 | Wilson |
| 5,522,832 A | * | 6/1996 | Kugo et al. ................ 606/185 |
| 5,531,701 A | * | 7/1996 | Luther ................ 604/165.04 |
| 5,700,250 A | * | 12/1997 | Erskine .................... 604/263 |
| 6,007,519 A | | 12/1999 | Rosselli |
| 2004/0044313 A1 | | 3/2004 | Nakajima |

FOREIGN PATENT DOCUMENTS

| | | |
|---|---|---|
| CN | 1708325 A | 12/2005 |
| JP | 2000-254225 A | 9/2000 |
| JP | 2004-24622 A | 1/2004 |
| WO | WO 93/05832 A | 4/1993 |
| WO | WO 94/23785 A | 10/1994 |
| WO | WO 2004/030733 A | 4/2004 |

OTHER PUBLICATIONS

Chinese Patent Office Action for Application No. 200710160802.9, Apr. 15, 2011.

* cited by examiner

*Primary Examiner* — Nicholas D Lucchesi
*Assistant Examiner* — Leah Stohr
(74) *Attorney, Agent, or Firm* — Smith Patent Office

(57) ABSTRACT

An indwelling needle assembly usable in combination with an infusion system for infusion into a patient's body is disclosed. The indwelling needle assembly is comprised of a needle having a needlepoint insertable into the patient's body; a sleeve slidably fitted on the needle; a catheter including a catheter tube slidably fitted on the sleeve; a base body fixed to a proximal end of the needle; and a slider fixed to the sleeve and slidably engaged with the base body so as to be movable between a first position to have the needlepoint projecting out of the sleeve and a second position to have the needlepoint retracted in the sleeve, wherein the needle, the sleeve, the base body and the slider are unitarily extractable from the catheter.

18 Claims, 10 Drawing Sheets

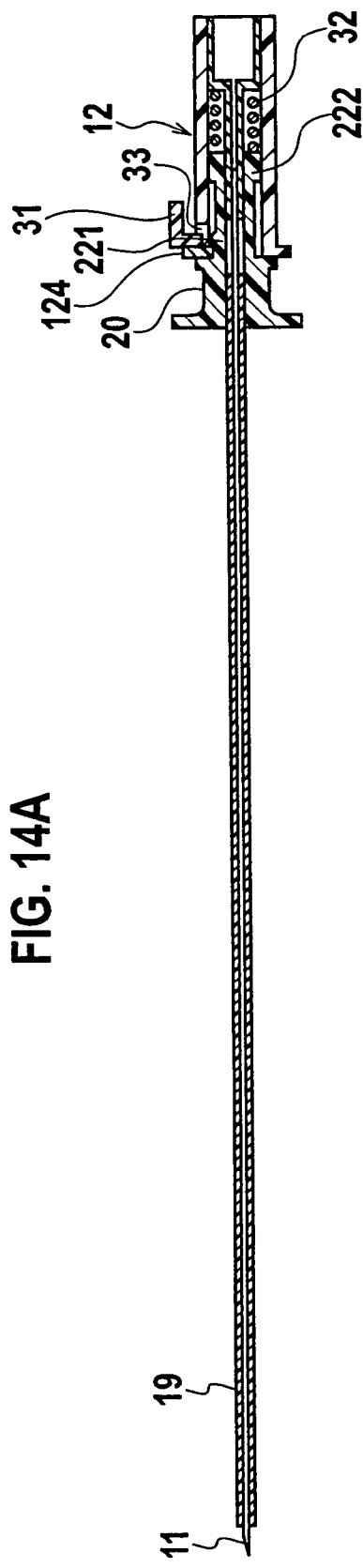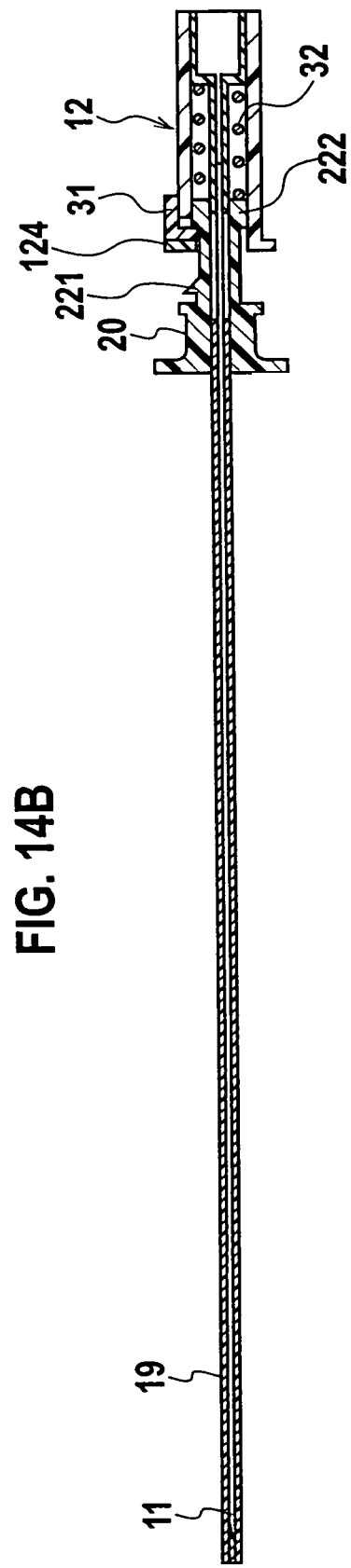

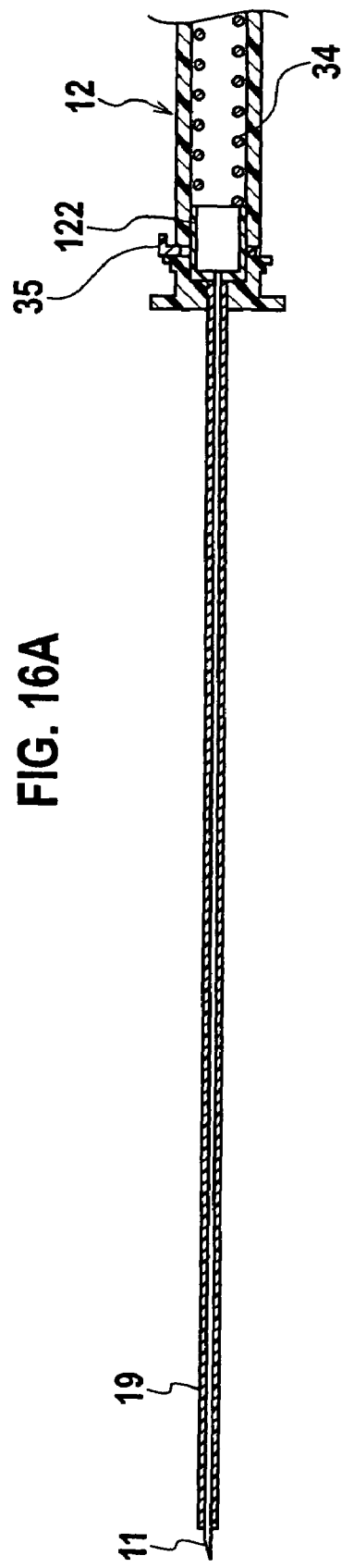
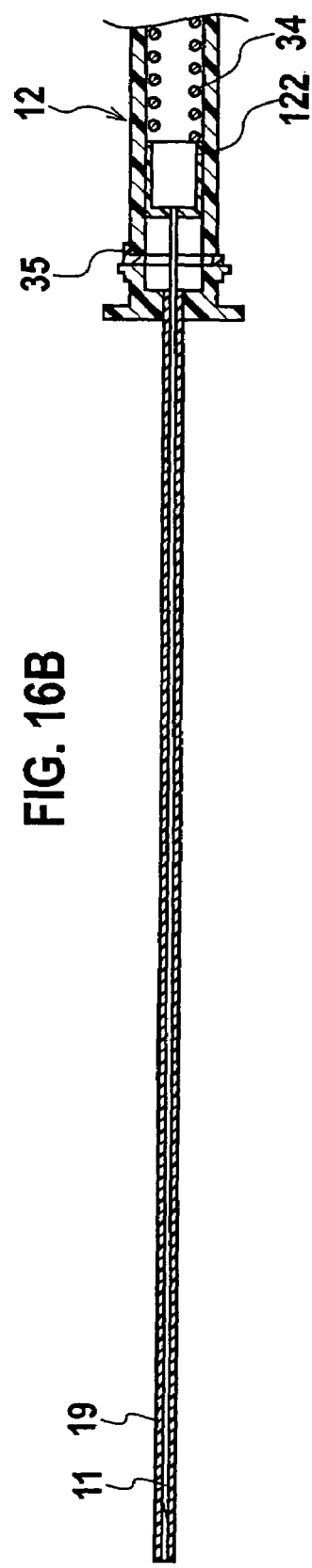

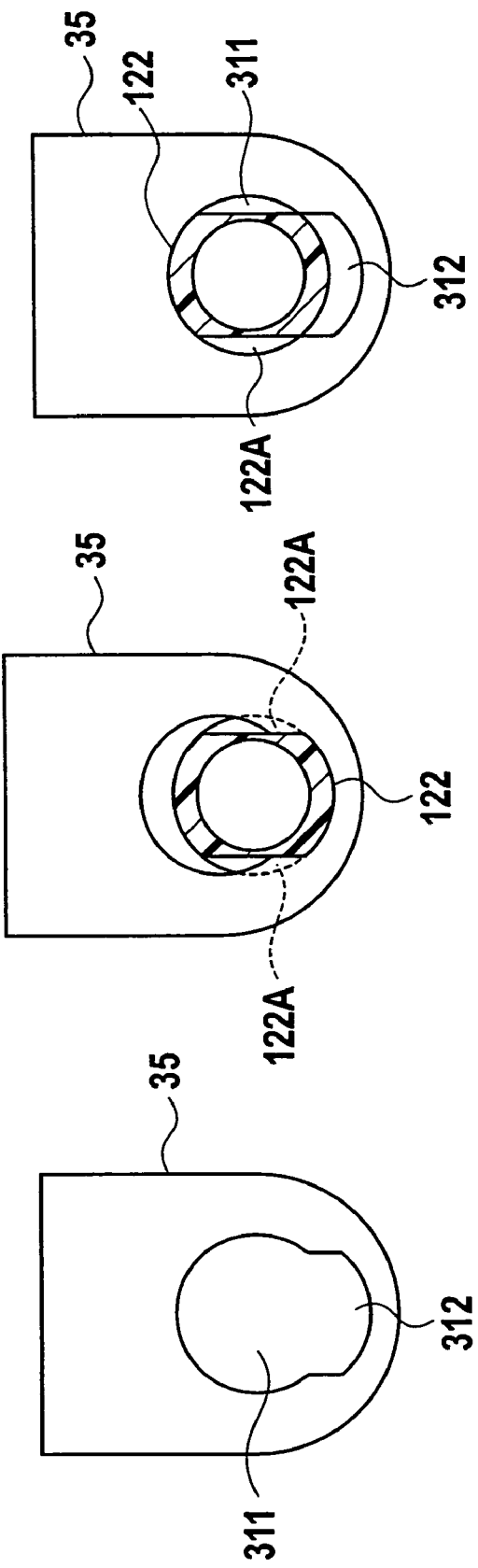

INDWELLING NEEDLE ASSEMBLY

CROSS-REFERENCE TO RELATED APPLICATIONS

This application claims priorities from Japanese Patent Applications No. 2006-340501 filed on Dec. 18, 2006 and No. 2007-319259 filed on Dec. 11, 2007; the entire contents of which are incorporated herein by reference.

BACKGROUND OF THE INVENTION

1. Field of the Invention

The present invention relates to an indwelling needle assembly usable for introducing a catheter into a vascular system of a patient at a time of infusion.

2. Description of the Related Art

A catheter is a thin tubular medical device or any device including a thin tube used to permit infusion or withdrawal of fluid into a vascular system or any cavity of a patient's body. To introduce such a catheter into a vascular system of a patient, a needle assembly with a needle slidably fitted in the catheter is frequently used. A medical personnel pierces a patient's body with the needle along with the catheter. Thereafter the needle may be extracted but the catheter is left indwelled in the patient's body. The catheter is connected to an infusion device and thereby comes to be available for infusion. Some needle assemblies are comprised of telescopically extensible sleeves as a safety guard for covering the needles so as to prevent accidental sticking.

SUMMARY OF THE INVENTION

Nowadays medical devices are desired to reduce loads on patients. Reduction in diameter of the needle may be a latent solution to reduction of a pain at a time of piercing the patient's body. However, the thinner the needle is formed, the more the needle is susceptible to buckling. Further, reduction in diameter of the needle necessarily leads to reduction in inner diameter of the catheter because the catheter must closely fit on the needle. Therefore, diameter of a needle of an indwelling needle assembly had a minimum limit in view from a practical standpoint.

The present invention is intended for providing an indwelling needle assembly with a safety guard, which enables application of a thinner needle than ever.

According to an aspect of the invention, an indwelling needle assembly is usable in combination with an infusion system for infusion into a patient's body. The indwelling needle assembly is comprised of: a needle having a needlepoint insertable into the patient's body; a sleeve slidably fitted on the needle; a catheter including a catheter tube slidably fitted on the sleeve; a base body fixed to a proximal end of the needle; and a slider fixed to the sleeve and slidably engaged with the base body so as to be movable between a first position to have the needlepoint projecting out of the sleeve and a second position to have the needlepoint retracted in the sleeve, wherein the needle, the sleeve, the base body and the slider are unitarily extractable from the catheter.

Preferably, the sleeve is comprised of a taper end or an obliquely cutoff end. The end projects from the catheter toward the needlepoint.

Preferably, the catheter is comprised of a distal end portion fitted on the needle, and a taper portion continuously tapering from the catheter tube toward the distal end portion. More preferably, the sleeve is so formed as to fill a space held between the needle and the catheter.

More preferably, the indwelling needle assembly is further comprised of a latch configured to hold the slider at the first position.

Still preferably, the indwelling needle assembly is further comprised of a stopper latch configured to stop the slider at the second position.

Further preferably, the indwelling needle assembly is further comprised of an elastic body configured to urge the slider toward the second position; and a release configured to release the slider from the first position, the release being fixed to the base body to allow operation from an exterior of the base body.

Still preferably, the sleeve is comprised of a first sleeve and a second sleeve fitting on the first sleeve.

Still preferably, the needle is comprised of a hollow piercing portion and a translucent body portion, and the sleeve is made of a translucent material.

BRIEF DESCRIPTION OF THE DRAWINGS

FIG. 4A shows a state of exposing the needlepoint and FIG. 4B shows a state of retracting the needlepoint;

FIGS. 14A and 14B are cross sectional view of a needle and its attachments extracted from a catheter in accordance with an eighth embodiment of the present invention, where FIG. 14A shows a state of exposing the needlepoint and FIG. 14B shows a state of retracting the needlepoint;

FIGS. 16A and 16B are cross sectional view of a needle and its attachments extracted from a catheter of the exemplary modification, where FIG. 16A shows a state of exposing the needlepoint and FIG. 16B shows a state of retracting the needlepoint; and FIGS. 17A-17C are side views of a needle base and a release button viewed in a direction along a longitudinal direction of the needle assembly.

DETAILED DESCRIPTION OF THE EXEMPLARY EMBODIMENTS

Exemplary embodiments of the present invention will be described hereinafter with reference to FIGS. 1 to 17C. Throughout the specification and claims, a relative term "distal" is defined and used as toward a needlepoint, and "proximal" is opposite thereto.

Indwelling needle assemblies described hereinafter are usable in combination with any infusion system for infusion into a patient's body.

First Embodiment

Figure 1:
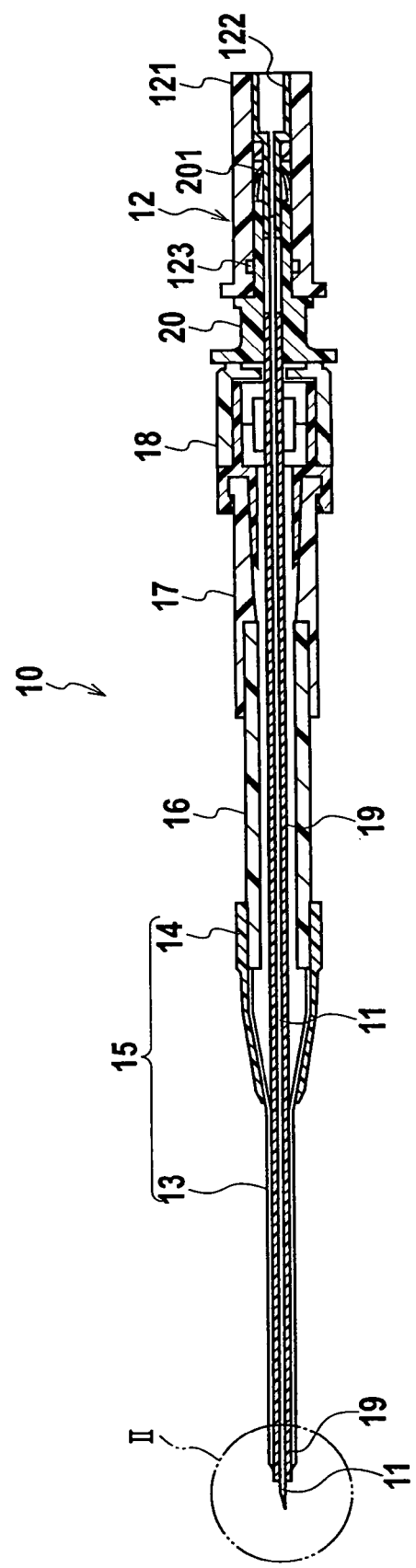
FIG. 1 is a cross sectional view of an indwelling needle assembly in accordance with a first embodiment of the present invention.

Referring to FIG. 1, an indwelling needle assembly 10 according to a first embodiment of the present invention is comprised of a needle 11 for piercing a patient's body, a base body 12 fixed to a proximal end of the needle 11, a sleeve 19 fitted on the needle 11, a slider 20 fixed to the sleeve 19, and a catheter 15 having a catheter tube 13 fitted on the sleeve 19.

The needle 11 is inserted in the sleeve 19 and the catheter 15. An outer diameter of the needle 11 is substantially corresponding to an inner diameter of the sleeve 19, thereby the needle 11 is fitted in and made slidable relative to the sleeve 19. The needle 11 may be made of, but not limited to, any metal such as stainless steels, aluminum, titanium or its alloys. The needle 11 has an enough length to have a needlepoint thereof projecting out of the sleeve 19 and the catheter 15. The needlepoint is an obliquely cutoff and sharp end of the needle 11 so as to enable piercing the patient's skin with small resistance. The diameter of the needle 11 should be preferably set smaller for the purpose of reducing a pain of piercing.

The base body 12 is comprised of a grip 121 which is used for handling the indwelling needle assembly 10, and a needle base 122 to which a proximal end of the needle 11 is fixed. The grip 121 is formed into a cylindrical shape and has a through hole therein. The needle base 122 is housed in the through hole of the grip 121 and is thereby fixed to the grip 121. The through hole of the grip 121 further houses an elastic latch 201 of a slider 20 described later. For the purpose of being latched by the elastic latch 201, the grip 121 is comprised of a groove 123 formed on the inner periphery of the through hole.

When a medical personnel pierce a patient's body with the needle 11, the medical personnel may use the base body 12 for handling. After piercing, the medical personnel can extract the base body 12 to detach the needle 11 from the indwelling needle assembly 10. Then the needle 11, the sleeve 19, the base body 12 and the slider 20 are unitarily extracted from the catheter 15. A hemostatic valve 18 is provided for the purpose of preventing blood from leaking out at the time of extracting.

The catheter 15 is comprised of the catheter tube 13 and a catheter adapter 14 for connection with the main body of the indwelling needle assembly 10. The catheter tube 13 should be made of any soft resin so as to avoid inflicting a blood vessel wall.

As the sleeve 19 closely fits on the needle 11, a total structure of the needle 11 and the sleeve 19 is reinforced and/or stiffened as compared with a structure of the needle 11 without the sleeve 19. Further, the sleeve 19 can slide relative to the needle 11 so that the needlepoint can be retracted in the sleeve 19. Details of these functions will be described hereinafter.

The sleeve 19 may be made of, but not limited to, any metals or resins. Further, translucent resins are more preferable. The sleeve 19 may be formed into a tube-like shape or, instead, a spiral shape enclosing the needle 11.

The slider 20 is formed into a short cylindrical shape having a flange. The slider 20 has a through hole which receives the needle 11 and a distal portion of the needle base 122 therein. A rear end of the sleeve 19 is inserted in the through hole and temporarily fixed. The slider 20 is further comprised of a pair of elastic latches 201 for engaging with the groove 123.

Narrowing the paired elastic latches 201 elastically, the slider 20 is inserted into the base body 12. Thereby the latches 201 have outward repulsive force. In accordance with this insertion, the distal portion of the needle base 122 is inserted into the through hole of the slider 20. Thereby the slider 20 is slidably engaged with the base body 12.

The indwelling needle assembly 10 is further comprised of a cramp tube 16 and a connector 17, both of which are interposed between the catheter 15 and the hemostatic valve 18. The needle 11 and the sleeve 19 penetrate, and are capable of being extracted from, the cramp tube 16, the connector 17 and the hemostatic valve 18, and then the cramp tube 16 is connected with the catheter adapter 14. The needle 11 and the sleeve 19 penetrate are capable of being extracted from the cramp tube 16, the connector 17 and the hemostatic valve 18. After extracting the needle 11 and the sleeve 19, the catheter 13 along with the cramp tube 16, the connector 17 and the hemostatic valve 18 is usually left indwelled.

As the sleeve 19 is fixed to the slider 20 and the needle 11 is fixed to the base body 12, positions of the slider 20 relative to the base body 12 regulates positional relation between the distal end of the sleeve 19 and the needlepoint of the needle 11. When the slider 20 is at an initial position, the slider 20 has the needlepoint projecting out of the sleeve 19. In contrast, when the slider 20 slightly moves toward the needlepoint and thereby reaches a next position where the latches 201 latch on the groove 123 of the grip 121, the slider 20 has the needlepoint retracted in the sleeve 19.

Figure 2:
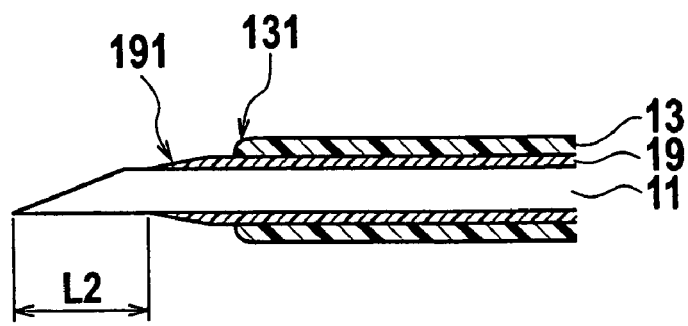
FIG. 2 is a partial cross sectional view of the indwelling needle assembly in which a portion II of FIG. 1 is magnified.

Referring to FIG. 2, the structure around the needlepoint will be described hereinafter.

The sleeve 19 has a taper end 191 projecting out from a distal end 131 of the catheter tube 13. The taper end 191 tapers toward the needlepoint. The needlepoint of the needle 11 projects out from the end 191 by a predetermined length L2 when the slider 20 is at the initial position.

Figure 3A:
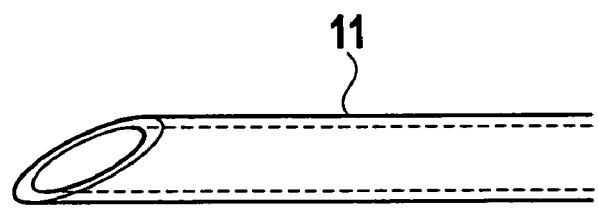
FIGS. 3A and 3B are perspective views around needle-points of hollow and solid-core needles applied to the indwelling needle assembly.
Figure 3B:
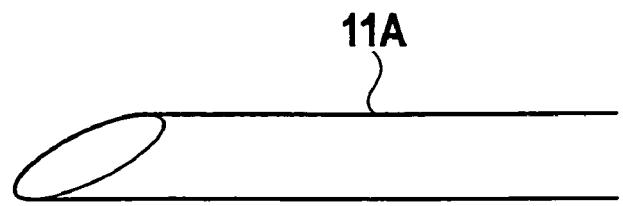

The needle 11 may be a hollow needle as shown in FIG. 3A or, alternatively, a solid-core needle 11A as shown in FIG. 3B.

Figure 4A:
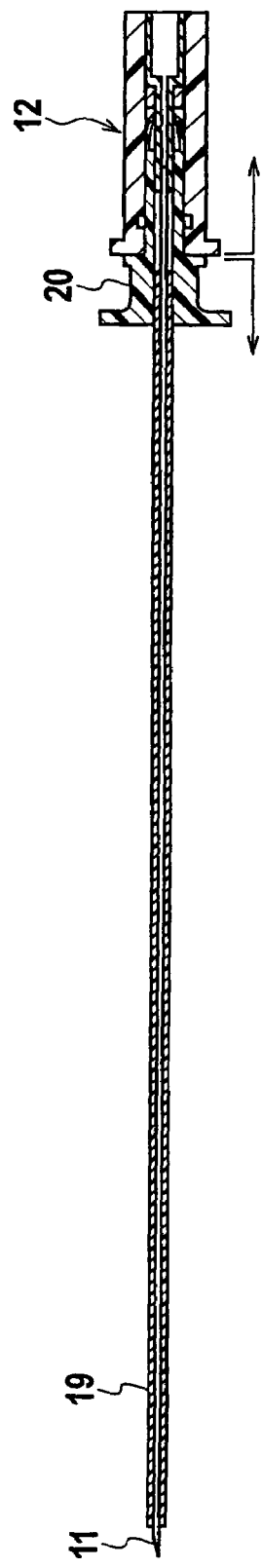
FIGS. 4A and 4B are cross sectional views of the needle and its attachments extracted from a catheter, where
Figure 4B:
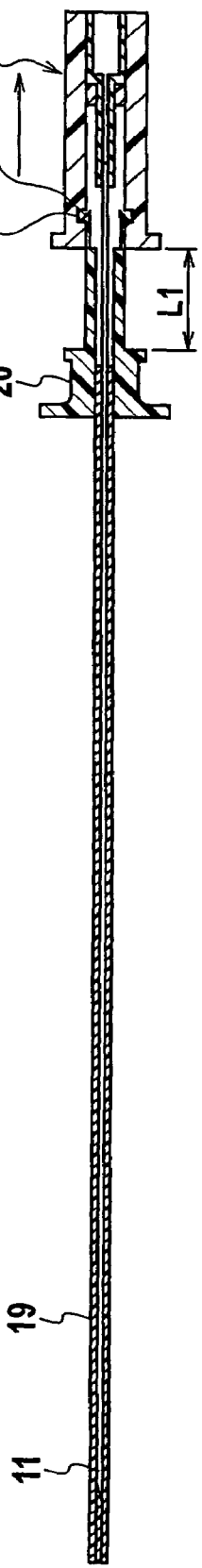

The extracted needle 11 is initially in a state shown in FIG. 4A. The needlepoint of the needle 11 is still projecting out of the sleeve 19. The medical personnel may then pick the base body 12 with fingers of one hand and can pick the slider 20 with finger of another hand. As the medical personnel slightly moves both hands to separate the slider 20 from the base body 12, the slider 20 moves toward the needlepoint. Then the needlepoint of the needle 11 is retracted in the sleeve 19 as shown in FIG. 4B.

When movement of the slider 20 reaches a length L1, the latches 201 come to the groove 123. Then the narrowed latches 201 widen outward by these own repulsive forces to latch on the groove 123. Thereby the slider 20 is held immovable relative to the base body 12. This state effectively prevents accidental sticking.

The aforementioned members are formed into a particular dimensional relation to satisfy the inequality of L1>L2. However, since L2 may be set into a very small value, L1 may be also set into a relatively small value. More specifically, the base body 12 is merely so structured as to allow small movement of the slider 20. Therefore, a compact structure may be applied to the assembly of the slider 20 and the base body 12.

When the needle 11 of the indwelling needle assembly 10 as structured as above is inserted into a vascular system of a patient, the catheter tube 13 accompanies the needle 11 and the sleeve 19 to enter into the vascular system. When the medical personnel verifies that the catheter tube 13 properly enters into the vascular system by a predetermined length, the medical personnel extracts the needle 11 and the sleeve 19 from the catheter 15. Then the catheter tube 13 is left indwelled in the vascular system. To start infusion, the hemostatic valve 18 is detached therefrom and an infusion system is connected to the connector 17.

As the sleeve 19 closely fits on the needle 11, a total structure of the needle 11 and the sleeve 19 is reinforced and/or stiffened. Therefore, even if the needle 11 is formed into a thinner shape, the needle 11 is insusceptible to buckling. More specifically, the aforementioned structure enables reduction in diameter of the needle 11 without deterioration of facility in piercing. Reduced diameter of the needle 11 leads to reduction of a pain at a time of piercing the patient's body as described above. Further, the taper end 191 of the sleeve 19 also reduces the pain.

The catheter tube 13 closely fits not on the needle 11 but on the sleeve 19. Therefore, even if the needle 11 is formed in a thin shape, the inner diameter of the catheter tube 13 is not necessarily reduced. As the catheter tube 13 can have a sufficient inner diameter, sufficient flow rate of an infusion fluid can be assured.

Second Embodiment

Figure 5:
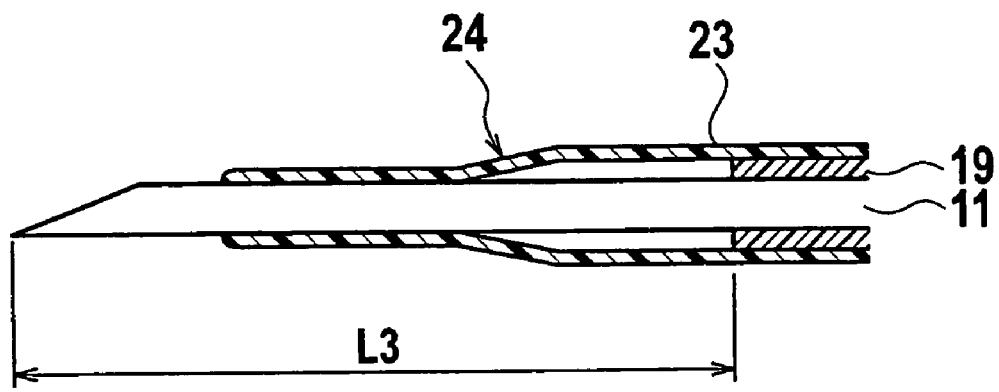
FIG. 5 is a partial cross sectional view of an indwelling needle assembly in accordance with a second embodiment of the present invention, in which a needlepoint is magnified.

The aforementioned first embodiment may be modified into a second embodiment described hereinafter. Referring to FIG. 5, a distal end of a catheter tube 23 is slightly elongated toward the needlepoint. The elongated distal end portion of the catheter tube 23 includes a taper portion 24 continuously smoothly tapering from the catheter tube 23 toward the distal end portion. Therefore, the distal end and its vicinity of the catheter tube 23 have smaller diameters than that of the remainder of the catheter tube 23. Further, the distal end portion fits on the needle 11. The distal end portion of the catheter tube 23 projects toward the needlepoint from the end of the sleeve 19 as shown in FIG. 5.

The needlepoint of the needle 11 projects out from the end of the sleeve 19 by a predetermined length L3 when the slider 20 is at the initial position. Also in this embodiment, related members are formed to have a particular dimensional relation to satisfy the inequality of L1>L3 so that movement of the slider 20 by a length L1 has the needlepoint retracted in sleeve 19.

The second embodiment also enables reduction in diameter of the needle 11 without deterioration of facility in piercing. Further, because the distal end portion of the catheter tube 23 fitting on the needle 11 and the taper portion 24 smoothly tapering enables smooth insertion of the catheter 15 along with the needle 11, a pain at a time of piercing the patient's body may be reduced.

Third Embodiment

Figure 6:
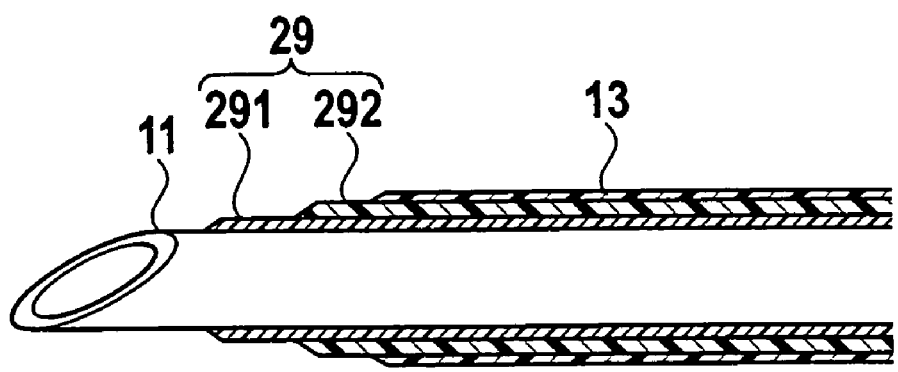
FIG. 6 is a partial cross sectional view of an indwelling needle assembly in accordance with a third embodiment of the present invention, in which a needlepoint is magnified.

The first embodiment may be modified into a third embodiment described hereinafter. According to the present embodiment, a sleeve 19 is comprised of a first sleeve 291 fitting on the needle 11 and a second sleeve 292 fitting on the first sleeve 291 as shown in FIG. 6. Respective ends of the first sleeve 291 and the second sleeve 292 are made into taper ends to reduce friction against the patient's skin.

The end of the second sleeve 292 slightly projects from the end of the catheter tube 13 and the end of the first sleeve 291 slightly projects from the end of the second sleeve 292. The needlepoint of the needle 11 projects out of the ends of the first sleeve 291 and the second sleeve 292. The catheter tube 13 may be comprised of a taper portion or, alternatively, may be formed to have a unitary diameter over the entire catheter tube 13. Further, the catheter tube 13 may be extended to cover ends of the first sleeve 291 and the second sleeve 292.

In accordance with the third embodiment, whereas the needlepoint and its vicinity are sufficiently thin, the remainder of the needle 11 is doubly reinforced and stiffened by the first sleeve 291 and the second sleeve 292 with sufficient thicknesses. While the structure of the needle 11 and its attachments provides sufficient strength and stiffness, the needle 11 gives small pain to a patient.

Fourth Embodiment

A fourth embodiment of the present invention will be described hereinafter with reference to FIGS. 7 and 8.

Figure 7:
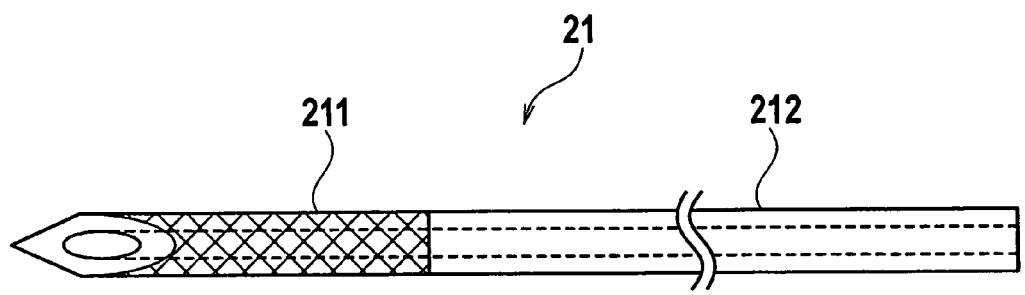
FIG. 7 is an elevational view of a needle in accordance with a fourth embodiment of the present invention.
Figure 8:
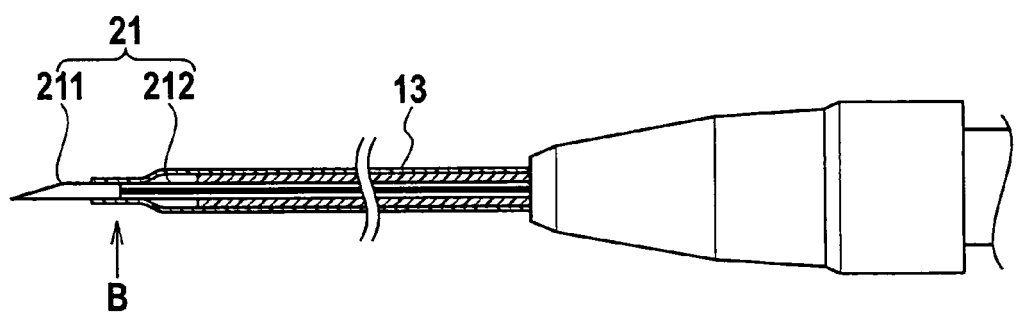
FIG. 8 is an elevational view of an indwelling needle assembly in accordance with the fourth embodiment as showing a gist thereof.

Referring to FIG. 7, a needle 21 of an indwelling needle assembly of the fourth embodiment is comprised of a head part 211 including a needlepoint for piercing, which is made of a metal, and a body part 212 connected with the head part 211.

The head part 211 is made into a short hollow needle. Examples of the metal applied to the head part 211 are stainless steels, aluminum, titanium and these alloys.

The body part 212 is a thin and long tube made of any translucent and relatively hard material to allow a visual check of blood flashback therethrough. As such a material, polystyrene, polyethylene and polypropylene may be exemplified.

The surface of the head part 211 should be smoothly continuous to the surface of the body part 212.

In accordance with the fourth embodiment, as soon as flashback of blood through the needle 21 passes a point B (see FIG. 8), the blood flashback becomes visible from the exterior. This may be applicable to visual check of whether the needle is properly positioned within the vascular system or not. In general, the part ranging from the point B to the catheter adapter 14 is not concealed by either the patient's skin or the medical personnel's hand in the course of the action of inserting the catheter tube 13 into the vascular system. Therefore, that this part is available for visual check is advantageous in view of easiness of checking properness of the position of the needle.

Fifth Embodiment

Figure 9:
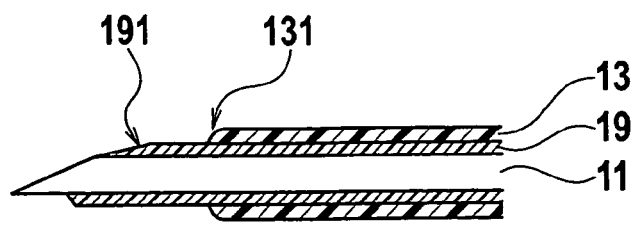
FIG. 9 is a partial cross sectional view of an indwelling needle assembly in accordance with a fifth embodiment of the present invention, in which a needlepoint is magnified.

A fifth embodiment of the present invention will be described hereinafter with reference to FIGS. 9 and 10.

In accordance with the fifth embodiment, a modification to the sleeve is made as compared with the first embodiment. The sleeve 19 of the fifth embodiment has a taper end 191 tapering toward the needlepoint and the taper end 191 is projecting out of the distal end of the catheter tube 13. The needlepoint of the needle 11 slightly projects from the taper end 191. The distal end of the catheter tube 13 has a rounded edge portion 131.

Figure 10:
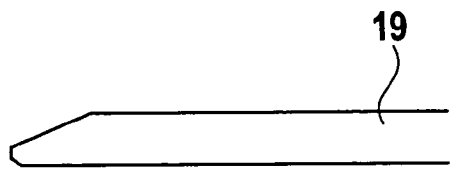
FIG. 10 is an elevational view of a sleeve in accordance with the fifth embodiment.

The taper end 191 is obliquely cut off as shown in FIG. 10. An utmost end of the taper end 191 may be rounded. More specifically, the taper end 191 has a shape similar to the needlepoint but its utmost end is so formed as not to obstruct piercing by the needlepoint.

The fifth embodiment further reduces a pain of piercing as the sleeve 19 is formed into the shape similar to the needlepoint.

Sixth Embodiment

Figure 11:
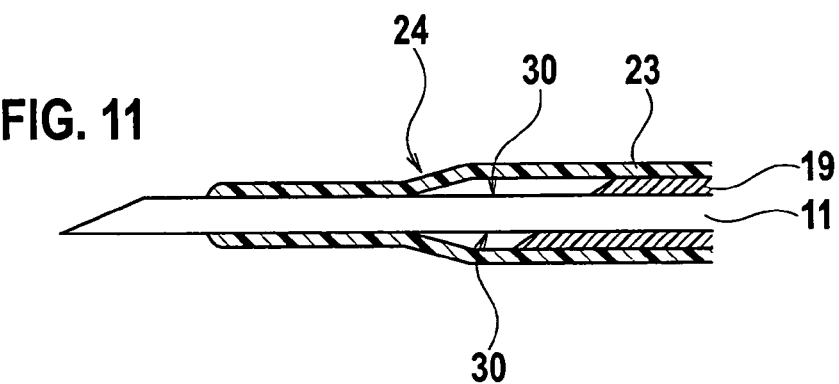
FIG. 11 is a partial cross sectional view of an indwelling needle assembly in accordance with a sixth embodiment of the present invention, in which a needlepoint is magnified.
Figure 12:
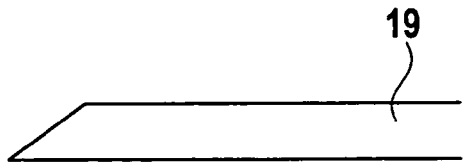
FIG. 12 is an elevational view of a sleeve in accordance with the sixth embodiment.

A sixth embodiment of the present invention will be described hereinafter with reference to FIGS. 11 and 12.

In accordance with the sixth embodiment, a modification to the catheter tube is made as compared with the above embodiments. The catheter tube 23 of the sixth embodiment has a taper portion 24 which continuously smoothly tapers from a main portion of the catheter tube 23 toward a distal end thereof. As a result of the tapering, the distal end and its vicinity may closely fit on the needle 11.

The sleeve 19 is retracted in the catheter tube 23. Further, the distal end of the sleeve 19 is obliquely cut off. The obliquely cutoff end is faced to the same direction of the oblique face of the needlepoint.

The present sixth embodiment, as similar to the second embodiment, enables smooth insertion of the catheter tube 23 along with the needle 11 because the sleeve 19 is covered with the catheter tube 23. This leads to reduction in a pain of piercing.

If a space 30 is held between the needle 11 and the catheter tube 23, because the catheter tube 23 is made of a soft material, a portion around the space 30 is susceptible to deformation. The deformation deteriorates easiness of piercing and increases a pain of piercing. The obliquely cutoff end reduces volume of the space 30, and thereby the deformation of the catheter tube 23 is suppressed. In particular, at a time of piercing, the needlepoint is oriented downward and therefore the cutoff face is correspondingly oriented. The space 30 at the side facing the patient's skin is relatively small. Therefore, deformation of the catheter tube 23 at the side facing to the patient's skin is suppressed. More specifically, the sixth embodiment improves easiness of piercing and reduces a pain of piercing.

Seventh Embodiment

Figure 13:
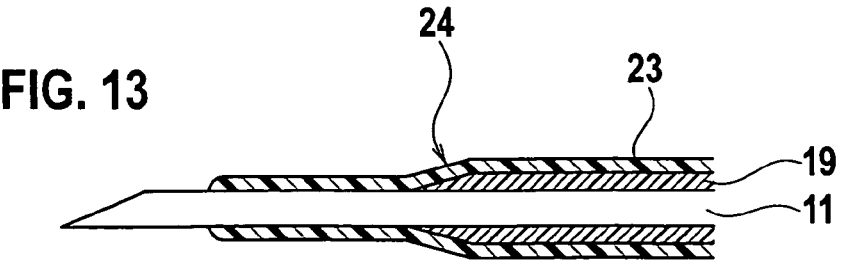
FIG. 13 is a partial cross sectional view of an indwelling needle assembly in accordance with a seventh embodiment of the present invention, in which a needlepoint is magnified.

A seventh embodiment of the present invention will be described hereinafter with reference to FIG. 13.

In accordance with the seventh embodiment, a modification to the catheter tube and the sleeve is made as compared with the above embodiments. The catheter tube 23 of the seventh embodiment has a taper portion 24 which tapers toward the needlepoint. Therefore, the distal end and its vicinity of the catheter tube 23 have smaller diameters than that of the remainder of the catheter tube 23. Further, the distal end portion of the catheter tube 23 fits on the needle 11. The sleeve 19 is retracted in the catheter tube 23.

The distal end of the sleeve 19 is so formed as to fill a space held between the needle 11 and the catheter tube 23.

The present seventh embodiment, as similar to the second embodiment, enables smooth insertion of the catheter tube 23 along with the needle 11 because the sleeve 19 is covered with the catheter tube 23. This leads to reduction in a pain of piercing.

Further, as the space held between the needle 11 and the catheter tube 23 is filled with the distal end of the sleeve 19, deformation of the catheter tube 23 caused by existence of the space is prevented. Therefore, the seventh embodiment improves easiness of piercing.

Eighth Embodiment

An eighth embodiment of the present invention will be described hereinafter with reference to FIGS. 14A and 14B.

In accordance with the present eighth embodiment, a means for actuating the slider is added. An elastic body 32 such as a spring is compressively interposed between the needle base and the slider 20 so as to urge the slider 20 to project outward (toward the needlepoint). Thereby, if the slider 20 is released from an initial position as shown in FIG. 14A, repulsive force of the elastic body (the spring) 32 moves the slider 20 toward the next position as shown in FIG. 14B without medical personnel's manual actuation.

Latching means may be also modified. The slider 20 may be comprised of a first latch 221 for holding the slider 20 at an initial position and a second latch 222 for latching on the slider 20 at a next position, instead of the pair of elastic latches 201 shown in FIGS. 4A and 4B. Further, according thereto, the base body 12 may be comprised of a hook 124 for catching the first latch 221 and a release button 31 capable of being pressed. The release button 31 has a projection projecting into the interior of the base body 12. The base body 12 is further comprised of an opening 33 through which the projection of the release button 31 projects into the interior.

Initially, the first latch 221 is caught by the hook 124, thereby the slider 20 is at the initial position where the needlepoint is made to project out of the sleeve 19. When the release button 31 is pressed down, the first latch 221 is pressed by the projection of the release button 31 and therefore goes beyond the hook 124. Then the slider 20 is released from the initial position and moved by the elastic body (the spring) 32 toward the next position where the needlepoint is made retracted in the sleeve 19. Then the second latch 222 is caught by the projection of the release button 31 so that the slider 20 is held at this position as shown in FIG. 14B.

The aforementioned means for actuating the slider may be further modified into another version as shown in FIGS. 15A-17C.

Figure 15B:
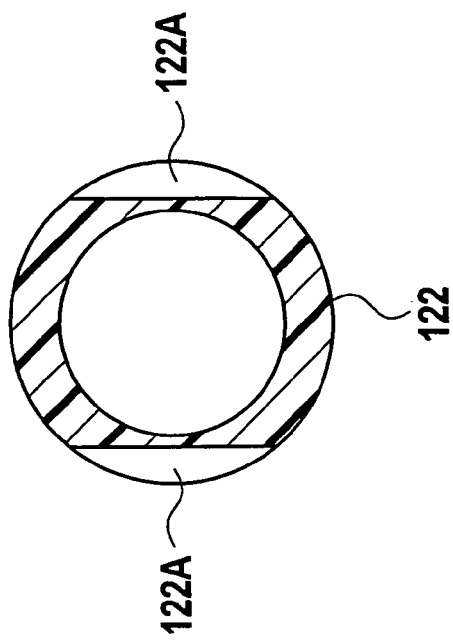
FIG. 15A is an elevational view of a needle base of an exemplary modification and FIG. 15B is a cross sectional view taken along a line XVB-XVB of FIG. 15A.
Figure 15A:
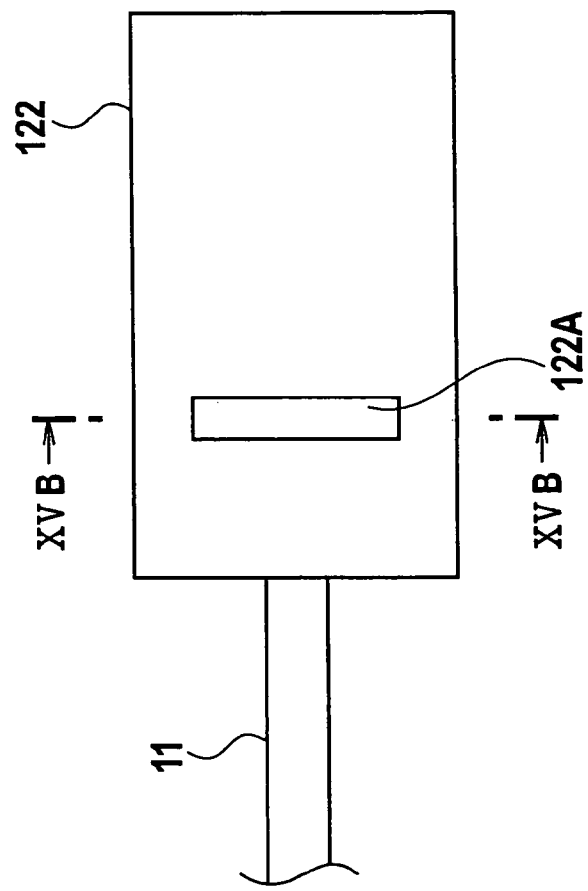

Referring to FIG. 15A, a pair of slots 122A are cut out from both sides of a needle base 122. Each cross section of the slots 122A has a shape defined by a straight line and an arc as shown in FIG. 15B.

A base body 12 used in combination with the needle base 122 is comprised of a release button 35 capable of being pressed. The release button 35 has a through hole 311 formed into a keyhole shape to have a short keyway 312 as shown in FIG. 17A.

The through hole 311 with the keyway 312 are so formed as to be engageable with the slots 122A of the needle base 122 when the release button 35 is not pressed down as shown in FIG. 17B. The through hole 311 is further so formed as to allow free movement of the needle base 122 therethrough when the release button 35 is fully pressed down as shown in FIG. 17C.

An elastic body 34 such as a spring is interposed between the needle base 122 and the base body 12 so as to draw the needle base 122 toward a direction where the needle 11 is retracted in the sleeve 19.

The needle base 122 and the base body 12 are initially in a state shown in FIG. 16A. The needle base 122 is engaged with the release button 35 as shown in FIG. 17B and the needlepoint of the needle 11 is still projecting out of the sleeve 19. When the release button 35 is pressed down, engagement between the needle base 122 and the release button 35 is canceled as shown in FIG. 17C and the needle base 122 is released from the aforementioned initial position. The elastic body (the spring) 34 moves the needle base 122 toward the next position as shown in FIG. 16B where the needlepoint of the needle 11 is retracted in the sleeve 19.

The present invention will be enabled by any of or any combination of the aforementioned exemplary embodiments.

Although the invention has been described above by reference to a certain embodiment of the invention, the invention is not limited to the embodiments described above. Modifications and variations of the embodiment described above will occur to those skilled in the art, in light of the above teachings.

What is claimed is:

1. An indwelling needle assembly usable in combination with an infusion system for infusion into a patient's body, the indwelling needle assembly comprising:
a needle having a needlepoint insertable into the patient's body;
a sleeve slidably fitted on the needle;
a catheter including a catheter tube slidably fitted on the sleeve;
a base body fixed to a proximal end of the needle; and
a slider fixed to the sleeve and slidably engaged with the base body so as to be movable between a first position to have the needlepoint projecting out of the sleeve and a second position to have the needlepoint retracted in the sleeve,
wherein the needle, the sleeve, the base body and the slider are unitarily extractable from the catheter,
wherein the sleeve includes an obliquely cutoff flat end, and the obliquely cutoff flat end projects from the catheter toward the needlepoint, and
wherein the catheter includes a distal end portion directly fitted on the needle, and a taper portion continuously tapering from the catheter tube toward the distal end portion.

2. The indwelling needle assembly of claim 1, wherein the sleeve is so formed as to fill a space held between the needle and the catheter.

3. The indwelling needle assembly of claim 1, further comprising:
a latch configured to hold the slider at the first position.

4. The indwelling needle assembly of claim 1, further comprising:
a stopper latch configured to stop the slider at the second position.

5. The indwelling needle assembly of claim 3, further comprising:
an elastic body configured to urge the slider toward the second position; and
a release configured to release the slider from the first position, the release being fixed to the base body to allow operation from an exterior of the base body.

6. The indwelling needle assembly of claim 1, wherein the sleeve includes a first portion and a second portion fitting on the first portion.

7. The indwelling needle assembly of claim 1, wherein the needle includes a hollow piercing portion and a translucent body portion, and the sleeve includes a translucent material.

8. An indwelling needle assembly usable in combination with an infusion system for infusion into a patient's body, the indwelling needle assembly comprising:
a needle having a needlepoint insertable into the patient's body;
a sleeve slidably fitted on the needle;
a catheter including a catheter tube slidably fitted on the sleeve, a distal end portion directly fitted on the needle, and a taper portion continuously tapering from the catheter tube toward the distal end portion;
a base body fixed to a proximal end of the needle; and
a slider fixed to the sleeve and slidably engaged with the base body so as to be movable between a first position to have the needlepoint projecting out of the sleeve and a second position to have the needlepoint retracted in the sleeve,
wherein the needle, the sleeve, the base body and the slider are unitarily extractable from the catheter; and
wherein the needle, the sleeve and the catheter are so dimensioned as to enter into the patient's body.

9. The indwelling needle assembly of claim 8, wherein the sleeve includes an end selected from the group of a tapered end and an obliquely cutoff flat end, the end projecting from the catheter toward the needlepoint.

10. The indwelling needle assembly of claim 8, wherein the sleeve is so formed as to fill a space held between the needle and the catheter.

11. The indwelling needle assembly of claim 8, further comprising:
a latch configured to hold the slider at the first position.

12. The indwelling needle assembly of claim 8, further comprising:
a stopper latch configured to stop the slider at the second position.

13. The indwelling needle assembly of claim 11, further comprising:
an elastic body configured to urge the slider toward the second position; and
a release configured to release the slider from the first position, the release being fixed to the base body to allow operation from an exterior of the base body.

14. The indwelling needle assembly of claim 8, wherein the sleeve includes a first portion and a second portion fitting on the first portion.

15. The indwelling needle assembly of claim 8, wherein the needle includes a hollow piercing portion and a translucent body portion, and the sleeve includes a translucent material.

16. An indwelling needle assembly usable in combination with an infusion system for infusion into a body, the indwelling needle assembly comprising:
a needle having a needlepoint insertable into the body;
a sleeve slidably fitted on the needle;
a catheter including a catheter tube slidably fitted on the sleeve;
a base body fixed to a proximal end of the needle; and
a slider fixed to the sleeve and slidably engaged with the base body so as to be movable between a first position to have the needlepoint projecting out of the sleeve and a second position to have the needlepoint retracted in the sleeve,
wherein the catheter includes a distal end portion directly fitted on the needle, and a taper portion continuously tapering from the catheter tube toward the distal end portion,
wherein the needle, the sleeve, the base body and the slider are unitarily extractable from the catheter,
wherein the sleeve includes a first surface parallel to an outer surface of the needle and a second surface formed in a flat shape and adjacent to the first surface so that an oblique angle is formed between the first surface and the second surface.

17. The indwelling needle assembly of claim 16, wherein the sleeve includes a third surface formed at an end surface of the sleeve and the second surface extends to the third surface of the sleeve.

18. The indwelling needle assembly of claim 17, wherein a portion of the third surface of the sleeve has a rounded shape.

* * * * *